(12) United States Patent
Wang et al.

(10) Patent No.: US 6,235,310 B1
(45) Date of Patent: May 22, 2001

(54) METHODS OF DELIVERY USING CATIONIC LIPIDS AND HELPER LIPIDS

(75) Inventors: Jinkang Wang, San Francisco; Yi-Lin Zhang, San Mateo, both of CA (US)

(73) Assignee: Valentis, Inc., Burlingame, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/054,769

(22) Filed: Apr. 3, 1998

Related U.S. Application Data

(60) Provisional application No. 60/088,359, filed on Apr. 4, 1997.

(51) Int. Cl.[7] .......................... A61K 9/127; A61K 9/133
(52) U.S. Cl. ........................ 424/450; 424/943; 935/54
(58) Field of Search .................... 424/450, 1.21, 424/9.321, 9.51, 417, 94.3, 812; 935/54; 436/829

(56) References Cited

U.S. PATENT DOCUMENTS

| | | |
|---|---|---|
| 5,264,618 | 11/1993 | Felgner et al. |
| 5,279,833 * | 1/1994 | Rose ........................ 424/450 |
| 5,550,289 | 8/1996 | Eppstein et al. |
| 5,650,096 * | 7/1997 | Harris ........................ 252/357 |

FOREIGN PATENT DOCUMENTS

| | | |
|---|---|---|
| 0 795 325 | 9/1997 | (EP). |
| WO 93/12756 | 7/1993 | (WO). |
| WO 93/25673 | 12/1993 | (WO). |
| WO 95/14380 | 6/1995 | (WO). |
| WO 95/14381 | 6/1995 | (WO). |
| WO 95/14651 | 6/1995 | (WO). |
| WO 95/35301 | 12/1995 | (WO). |
| WO 96/40962 | 12/1996 | (WO). |
| WO 96/40963 | 12/1996 | (WO). |
| WO 97/00241 | 1/1997 | (WO). |
| WO 97/46223 | 12/1997 | (WO). |

OTHER PUBLICATIONS

Hug in BBA 1097, p 1–17, 1991.*
Felgner et al. (1994), "Enhanced Gene Delivery and Mechanism Studies with a Novel Series of Cationic Lipid Formulations," *Journal of Biological Chemistry*, vol. 269, No. 4, pp. 2550–2561.
Sumida et al., *Chemical Abstracts*, vol. 120, No. 24, Jun. 13, 1994, abstract No. 307101.
Alton et al., (1993), *Nat. Genet.*, vol. 5, pp. 135–142.
Behr et al., (1989), *Proc. Natl. Acad. Sci.* (USA), vol. 86, pp. 6982–69.
Debs et al., (1990), *J. Biol. Chem.*, vol. 265, pp. 10189–10192.
Eibl and Wooley, (1979), *Biophys. Chem.*, vol. 10, pp. 261–271.
Eibl, (1980), "Synthesis of Glycerophospholipids," *Chemistry and Physics of Lipids*, vol. 26, pp. 405–429.
Farhood et al., (1992), *Biochim. Biophys. Acta*, vol. 1111, pp. 239–246.

(List continued on next page.)

Primary Examiner—Gollamudi S. Kishore
(74) Attorney, Agent, or Firm—McDonnell Boehnen Hulbert & Berghoff

(57) ABSTRACT

Methods and compositions are provided for the introduction of polyanionic molecules, in particular, nucleic acids, into mammalian cells using certain phosphatidyl ethanolamines as helper lipids in conjunction with various cationic lipids. In particular, cationic lipid-mediated transfection of mammalian cells is improved by the use of lipid carriers comprising DLPE or DiPPE and cationic lipids.

40 Claims, 9 Drawing Sheets

OTHER PUBLICATIONS

Felgner et al., (1987), *Proc. Natl. Acad. Sci.* (USA), vol. 84, pp. 7413–7417.

Felgner et al., (1994), *J. Biol Chem.*, vol. 269, No. 4, pp. 2550–2561.

Gao and Huang, (1991), *Biochem. Biophys. Res. Comm.*, vol. 179, pp. 280–285.

Hofland et al., (1996), *Proc. Natl. Acad. Sci.* (USA), vol. 93, pp. 7305–7309.

Hui et al., (1996), *Biophys. J.*, vol. 71, pp. 590–599.

Lasic and Templeton, (1996), *Adv. Drug Deliv. Rev.*, vol. 20, pp. 221–266.

Liu et al., (1997), *Nature Biotech.*, vol. 15, pp. 167–173.

Malone et al., (1989), *Proc. Natl. Acad. Sci.* (USA), vol. 86, pp. 6077–6081.

Rose et al., (1991), *BioTechniques*, vol. 10, No. 4, pp. 520–525.

Semple et al., (1996), *Biochem.*, vol. 35, No. 8, pp. 2521–2525.

Solodin et al., (1995), *Biochem.*, vol. 34, No. 41, pp. 13537–13544.

Stribling et al., (1992), *Proc. Natl. Acad. Sci.* (USA), vol. 89, pp. 11277–11281.

Vigneron et al., (1996), *Proc. Natl. Acad. Sci.* (USA), vol. 93, pp. 9682–9686.

von der Leyen et al., (1995), *Proc. Natl. Acad. Sci.* (USA), vol. 92, pp. 1137–1141.

Zhu et al., (1993), *Science*, vol. 261, pp. 209–211.

Leventis and Silvius, (1990), *Bichem. Biophys. Acta.*, 1023(1):124–132.

Wheeler et al., (1996), *Biochim. Biophys. Acta.*, 1280:1–11.

* cited by examiner

DLPE

DMPE

DPPE

Dipalmitoloeoyl-PE

Diphytanoyl-PE

DSPE

DOPE

Dielaidoyl-PE

Dilinoleoyl-PE

METHODS OF DELIVERY USING CATIONIC LIPIDS AND HELPER LIPIDS

CROSS-REFERENCE

This application is a continuation-in-part of U.S. provisional application Ser. No. 60/088,359, filed Apr. 4, 1997.

FIELD OF THE INVENTION

This invention relates to helper lipids, used in conjunction with cationic lipids, for the preparation of liposomes and other lipid-containing carriers of nucleic acids and other substances, for delivery to cells. In particular, the invention relates to the use of certain phosphatidylethanolamines as helper lipids for improving cationic-lipid mediated nucleic acid delivery.

BACKGROUND OF THE INVENTION

A number of lipid-based materials such as liposomes have been used as biological carriers for many pharmaceutical and other biological applications, particularly to introduce drugs, radiotherapeutic agents, enzymes, viruses, transcriptional factors and other cellular vectors into a variety of cultured cell lines and animals. Clinical trials have demonstrated the effectiveness of liposome-mediated drug delivery for targeting liposome-entrapped drugs to specific tissues and specific cell types. See, for example, U.S. Pat. No. 5,264,618, which describes techniques for using lipid carriers, including the preparation of liposomes and pharmaceutical compositions and the use of such compositions in clinical situations.

More recently, cationic lipids have been used to deliver nucleic acids to cells, allowing uptake and expression of foreign genes. In particular, cationic lipid-mediated delivery of exogenous nucleic acids in vivo in humans and/or various commercially important animals will ultimately permit the prevention, amelioration and cure of many important diseases and the development of animals with commercially important characteristics. The exogenous genetic material, either DNA or RNA, may provide a functional gene which, when expressed, produces a protein lacking in the cell or produced in insufficient amounts, or may provide an antisense RNA or ribozyme to interfere with a cellular function in, e.g., a virus-infected cell or a cancer cell, thereby providing an effective therapeutic for a disease state.

Nucleic acids are generally large polyanionic molecules which, therefore, bind cationic lipids through charge interactions. While lipid carriers have been shown to enhance nucleic acid delivery in vitro and in vivo, the mechanism by which they facilitate transfection is not clearly understood. While it was initially believed that lipid carriers indicated transfection by promoting fusion with plasma membranes, allowing delivery of the DNA complex into the cytoplasm, it is now generally accepted that the primary mechanism of cellular uptake is by endocytosis.

While the mechanism by which cationic lipid carriers act to mediate transfection is not clearly understood, they are postulated to act in a number of ways with respect to both cellular uptake and intracellular trafficking. Some of the proposed mechanisms by which cationic lipids enhance transfection include: (i) compacting the DNA, protecting it from nuclease degradation and enhancing receptor-mediated uptake, (ii) improving association with negatively-charged cellular membranes by giving the complexes a positive charge, (iii) promoting fusion with endosomal membranes facilitating the release of complexes from endosomal compartments, and (iv) enhancing transport from the cytoplasm to the nucleus where DNA may be transcribed. When used for in vivo delivery, the role of the cationic lipid carriers is further complicated by the interactions between the lipid-nucleic acid complexes and host factors, e.g., the effects of the lipids on binding of blood proteins, clearance and/or destabilization of the complexes.

Typically, cationic lipids are mixed with a non-cationic lipid, usually a neutral lipid, and allowed to form stable liposomes, which liposomes are then mixed with the nucleic acid to be delivered. The liposomes may be large unilamellar vesicles (LUVs), multilamellar vesicles (MLVs) or small unilamellar vesicles (SUVs). The liposomes are mixed with nucleic acid in solution, at concentrations and ratios optimized for the target cells to be transfected, to form cationic lipid-nucleic acid transfection complexes. Alterations in the lipid formulation and mode of delivery allow preferential delivery of nucleic acids to particular tissues in vivo. PCT patent application numbers WO 96/40962, WO 96/40963.

The majority of studies on cationic lipid-mediated delivery have focused on the cationic lipid component, with relatively little work aimed at the role of non-cationic co-lipids (also called helper lipids). A commonly used helper lipid is dioleoylphosphatidylethanolamine (DOPE). DOPE was shown to improve transfection efficiencies in vitro when used in conjunction with a number of different cationic lipids. Felgner et al., (1994) Proc. Natl. Acad. Sci. (USA) 269(4):2550–2561. It has been commonly believed that DOPE improved transfection by making the liposomes more fusogenic, thereby improving either fusion with the plasma membrane, fusion with the endosomal membrane, or both. However, the studies describing the role of DOPE as a neutral lipid were performed in vitro and did not address its effect in vivo. Other studies have shown that in vitro transfection results are not predictive of in vivo transfection and, therefore, lipid formulations that were optimized for in vitro transfection were not necessarily optimal in vivo. Recent reports have obtained improved in vivo transfection efficiencies using cholesterol as the helper lipid. Liu et al., (1997) Nature Biotech. 15: 167–173; Solodin et al., (1995) Biochem. 34(41): 13537–13544.

While the use of cationic lipid carriers for transfection is well-known, structure activity relationships are not well understood. It is postulated that different lipid carriers will affect each of the various steps in the transfection process (e.g., condensation, uptake, nuclease protection, endosomal release, nuclear trafficking, and decomplexation) with greater or lesser efficiency, thereby making the overall transfection rate difficult to correlate with lipid structures. Thus, alterations in either the cationic or helper lipid component do not have easily predictable effects on activity. For the most part, therefore, improvements to known cationic lipid-mediated delivery systems are dependent on empirical testing. When intended for in vivo transfection, new lipids and lipid formulations should be screened in vivo to accurately predict optimal lipids and formulations for transfection of target cells.

It is desirable to have improved lipid delivery systems, e.g., to achieve higher levels of in vivo gene transfection. Improved levels of gene transfection will allow the treatment of disease states for which higher levels of expression are needed for therapeutic effect than achievable with prior art lipid delivery systems. Alternatively, higher transfection levels allow use of smaller amounts of material to achieve comparable expression levels, thereby decreasing potential lipid-associated toxicities and decreasing cost. Further, by choice of neutral lipid, the toxicity of particular cationic lipids can be decreased. The present invention provides these and related advantages as well.

RELEVANT LITERATURE

Cationic lipid carriers have been shown to mediate intracellular delivery of plasmid DNA (Felgner et al., (1987) Proc. Natl. Acad. Sci. (USA), 84:7413–7416); mRNA (Malone et al., (1989) Proc. Natl. Acad. Sci. (USA) 86:6077–6081); and purified transcription factors (Debs et al., (1990) J. Biol. Chem. 265:10189–10192), in functional form. Literature describing the use of lipids as carriers for DNA include the following: Zhu et al., (1993) Science, 261:209–211; Vigneron et al., (1996) Proc. Natl. Acad. Sci. USA, 93:9682–9686; Hofland et al., (1996) Proc. Natl. Acad. Sci. USA, 93:7305–7309; Alton et al., (1993) Nat. Genet. 5:135–142; von der Leyen et al., (1995) Proc. Natl. Acad. Sci. (USA), 92:1137–1141; See also Stribling et al., (1992) Proc. Natl. Acad. Sci (USA) 89:11277–11281, which reports the use of lipids as carriers for aerosol gene delivery to the lungs of mice. For a review of liposomes in gene therapy, see Lasic and Templeton, (1996) Adv. Drug Deliv. Rev. 20:221–266.

The role of helper lipids in cationic lipid-mediated gene delivery is described in Felgner et al., (1994) J. Biol. Chem. 269(4): 2550–2561 (describing improved transfection using DOPE); Hui et al., (1996) Biophys. J. 71: 590–599; and Wheeler et al., (1996) Biochim. Biophys. Acta 1280:1–11. The effect of cholesterol on liposomes in vivo is described in Semple et al., (1996) Biochem. 35(8): 2521–2525.

SUMMARY OF THE INVENTION

Lipid carrier compositions comprising a cationic lipid and certain neutral phosphatidyl ethanolamines are provided, for delivery polyanionic molecules to cells. The neutral lipid may be 1,2-dilauroyl-sn-glycero-3-phosphoethanolamine (DLPE) or 1,2-diphytanoyl-sn-glycero-3-phosphoethanolamine (DiPPE), as the sole neutral lipid or in combination with other neutral lipids. Of particular interest is the use of DLPE or DiPPE in conjunction with cationic lipids to deliver nucleic acid molecules in vivo. In another embodiment, liposomes are provided, comprising a cationic lipid and a neutral lipid, where the neutral lipid is DLPE or DiPPE, as the sole neutral lipid or in combination with other neutral lipids.

The liposomes are useful as carriers for nucleic acid molecules, particularly plasmid DNA, to cells, whereby the DNA is taken up by the cells in functional form. The plasmid DNA typically comprises a recombinant expression construct, the DNA encoding a transcription product and operatively linked regulatory elements, whereby the DNA is capable of transcription in the target cells. As used herein, the term "transcription product" is intended to encompass an RNA product resulting from transcription of a nucleic acid sequence, and includes RNA sequences that are not translated into protein (such as antisense RNA or ribozymes) as well as RNAs that are subsequently translated into polypeptides or proteins. Also included is the direct delivery of RNA molecules, e.g., antisense RNA or ribozymes.

The invention also provides methods of in vivo and in vitro transfection of a target cell with a nucleic acid of interest. The methods include delivery of cationic lipid-nucleic acid complexes to cells in vitro, or in vivo by various routes of administration, where the complexes include a cationic lipid and a neutral lipid selected from the group consisting of DLPE and DiPPE. Preferred means of in vivo delivery include intravenous administration, intraperitoneal administration and inhalation of aerosolized complexes. In preferred embodiments, the cationic lipid used in combination with DLPE is DOTIM, MBOP or DOTAP, and the cationic lipid and DLPE are used in molar ratios of about 3:1 to 1:3, most preferably, molar ratios of about 1:1. In further preferred embodiments, liposomes comprising DLPE are complexed to DNA in ratios ranging from about 6:1 to 1:20 μg DNA:nmole cationic lipid, most preferably ratios from 1:6 to 1:15 μg DNA:nmole cationic lipid.

Specific preferred embodiments of the present invention will become evident from the following more detailed description of certain preferred embodiments and the claims.

DESCRIPTION OF SPECIFIC EMBODIMENTS

Figure 1A:
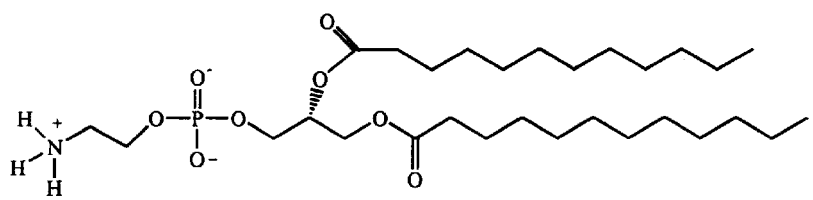
FIG. 1(a) and 1(b) show the chemical structures of nine phosphatidyl ethanolamine derivatives that were tested in combination with cationic lipids for the ability to transfect cells. This Figure includes a comparison of helper lipids with BODAI in transgene expression in lung following I.V. administration.
Figure 1A:
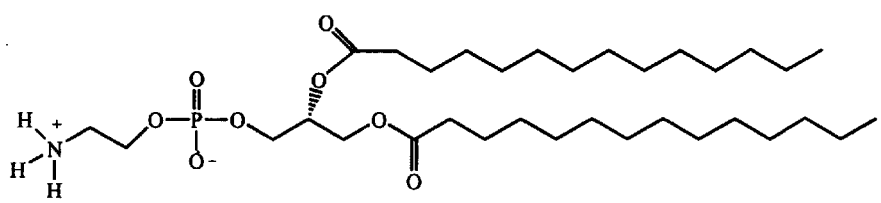
Figure 1A:
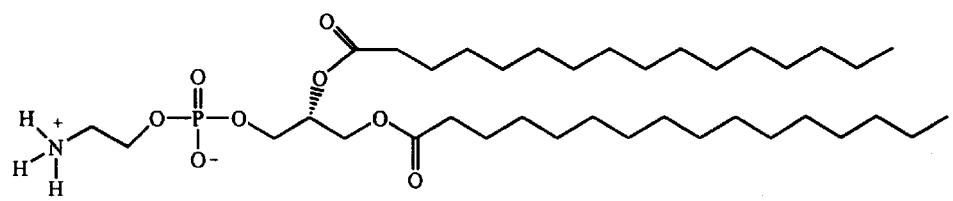
Figure 1A:
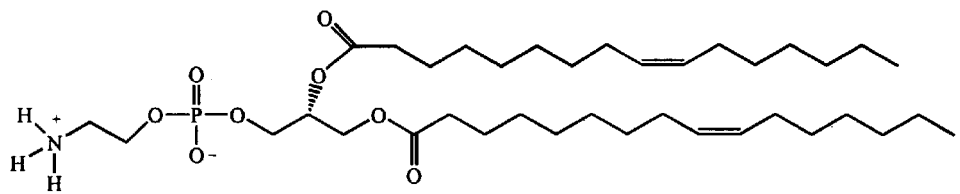
Figure 1A:
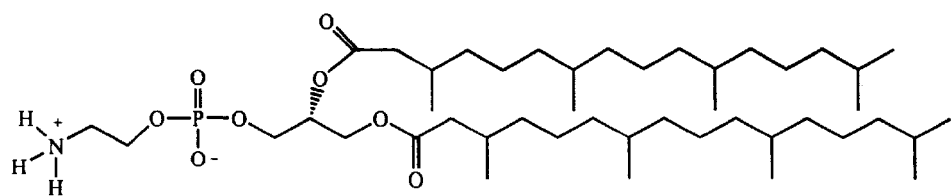
Figure 1B:
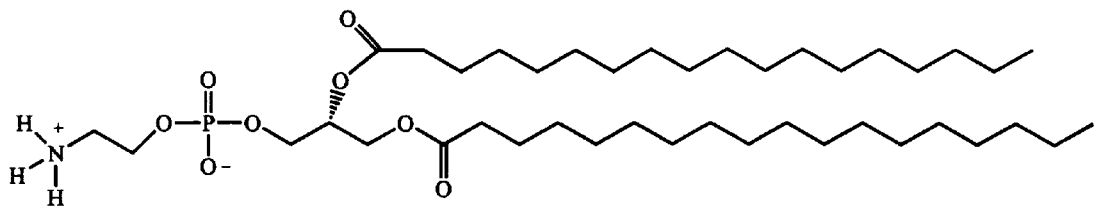
Figure 1B:
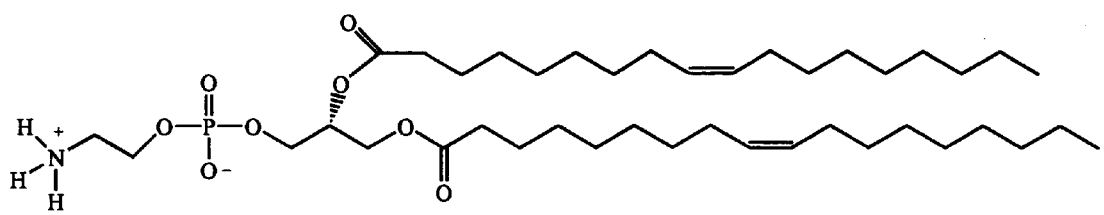
Figure 1B:
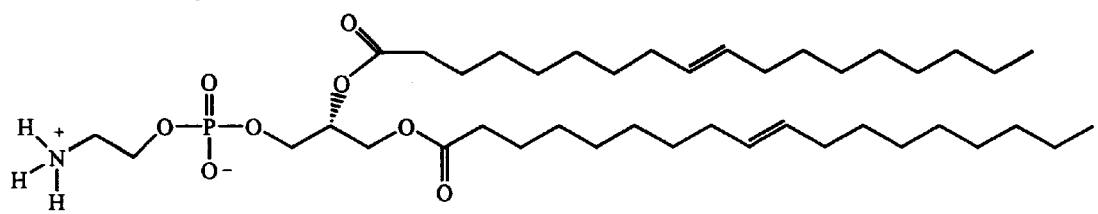
Figure 1B:
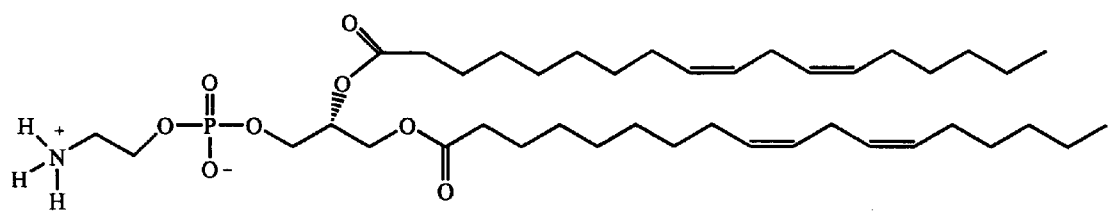

It has now been found that certain neutral lipids are useful as helper lipids in conjunction with cationic lipids for nucleic acid delivery, and can have a dramatic effect on gene expression levels. Useful neutral lipids include DLPE (1,2-dilauroyl-sn-glycero-3-phosphoethanolamine) and DiPPE (1,2-diphytanoyl-sn-glycero-3-phosphoethanolamine). These neutral lipids may be used as the sole neutral lipid, or in combination with one or more additional neutral lipids.

The lipid carrier (also called cationic lipid carrier) compositions of the invention are useful in any of the several applications in which cationic lipid carriers find use. For example, they may be used in standard drug delivery regimens, such as for the aerosolized delivery of antibiotics to the lungs of patients, or the topical application of various pharmaceutical formulations of creams, pastes, gels and the like. Lipid carrier compositions of the invention may be used as carriers for biologically active molecules such as antibiotics or nucleic acids in cell transfection processes. The compositions are particularly useful in the preparation of lipid carriers for nucleic acid delivery, mediating mammalian cell transfection in vitro and in vivo.

As used herein, "lipid carrier" or "cationic lipid carrier" refers to a lipid composition of one or more cationic lipids and one or more non-cationic lipids for delivering agents to cells. A cationic lipid carrier of the present invention includes as a helper lipid a neutral lipid selected from the group consisting of DLPE and DiPPE. The lipid carrier may be in any physical form including, e.g., liposomes, micelles, interleaved bilayers, etc.

The term "cationic lipid" is intended to encompass lipids that are positively charged at physiological pH, and more particularly, constituitively positively charged lipids comprising, for example, a quarternary ammonium salt moiety. Cationic lipids used for gene delivery typically consist of a hydrophilic polar head group and lipophilic aliphatic chains. Alternatively, cholesterol derivatives having a cationic polar head group are used in a similar manner. Farhood et al., (1992) Biochim. Biophys. Acta 1111:239–246; Vigneron et al., (1996) Proc. Natl. Acad. Sci. (USA) 93:9682–9686.

"Transfection" is intended to mean the delivery of exogenous nucleic acid molecules to a cell, either in vivo or in vitro, whereby the nucleic acid is taken up by the cell and is functional within the cell. A cell that has taken up the exogenous nucleic acid is referred to as a "host cell" or "transfected cell." A nucleic acid is functional within a host cell when it is capable of functioning as intended. Usually, the exogenous nucleic acid will comprise an expression cassette which includes DNA coding for a gene of interest, with appropriate regulatory elements, which will have the intended function if the DNA is transcribed and translated, thereby causing the host cell to produce the protein encoded therein. DNA may encode a protein lacking in the transfected cell, or produced in insufficient quantity or less active form, or secreted, where it ay have an effect on cells other than the transfected cell. Other examples of exogenous nucleic acid to be delivered include, e.g., antisense DNA or RNA, mRNA or ribozymes. Nucleic acids of interest also include DNA coding for a cellular factor which, when expressed, activates the expression of an endogenous gene.

"Transfection efficiency" refers to the relative number of cells of the total within a cell population that are transfected and/or to the level of expression obtained in the transfected cells. It will be understood by those of skill in the art that, by use of appropriate regulatory control elements such as promoters, enhancers and the like, the level of gene expression in a host cell can be modulated. The transfection efficiency necessary or desirable for a given purpose will depend on the purpose, for example the disease indication for which treatment is intended, and on the level of gene expression obtained in the transfected cells.

Lipid carriers usually contain a cationic lipid and a neutral lipid; most prior art lipid carriers contain DOPE or cholesterol as the neutral lipid. Most protocols involve forming liposomes made up of a mixture of cationic and neutral lipid. The neutral lipid is often helpful in maintaining a stable lipid bilayer in liposomes, and can significantly affect transfection efficiency. The liposomes may have a single lipid bilayer (unilamellar) or more than one bilayer (multilamellar). They are generally categorized according to size, where those having diameters up to about 50 to 80 nm are termed "small" and those greater than about 80 to 1000 nm, or larger, are termed "large." Thus liposomes are typically referred to as large unilamellar vesicles (LUVs), multilamellar vesicles (MLVs) or small unilamellar vesicles (SUVs).

The cationic liposomes are mixed with polyanionic compounds, and complexes form by charge interactions between the cationic lipid components and the negative charges of the polyanionic compounds. Polyanions of particular interest include nucleic acids, e.g., DNA, RNA or combinations of the two. "Cationic lipid-nucleic acid transfection complex" or "transfection complex" refers to a combination of a lipid carrier and a nucleic acid, in any physical form, for use in transfecting cells. A transfection complex may include additional moieties, e.g., targeting molecules such as receptor ligands or antibody fragments, or other accessory molecules such as, for example, transcription factors, polymerases, integrases, nuclear localizing peptides, and the like.

The nucleic acid may be in any physical form, e.g., linear, circular or supercoiled; single-stranded, double-, triple-, or quadruple-stranded; and further including those having naturally occurring nitrogenous bases and phosphodiester linkages as well as non-naturally occurring bases and linkages, e.g. for stabilization purposes. Preferably it is in the form of supercoiled plasmid DNA. Plasmid DNA is conveniently used for DNA transfections since there are no size constraints on the DNA sequences that may be included, and it can be produced in large quantity by growing and purifying it from bacterial cells. The cationic lipid carriers and polynucleotide molecules are mixed, resulting in cationic lipid-polynucleotide transfection complexes, the physical structure of which depends on the lipid and nucleic acid components, the ratios between them, concentrations, mixing conditions and the like. The lipids are mixed with nucleic acids in solution, at concentrations and ratios optimized for the target cells to be transfected. The process of forming cationic lipid-nucleic acid transfection complexes is generally as described in PCT patent application number WO 93/25673. For in vivo administration, care is taken to prevent complex aggregation.

DLPE and DiPPE are commercially available, e.g., from Avanti Polar Lipids (Alabaster, Ala.). Alternatively, they may be synthesized by methods known in the art. Several methods are described, e.g., in Eibl, (1980) "Synthesis of Glycerophospholipids," *Chemistry and Physics of Lipids*, 26:405–429. See also the references cited therein. For instance, DLPE may be synthesized starting from 1,2-dilauroylglycerol. Phosphorylation may be achieved by subsequent reactions with phosphorous oxychloride and t-butyloxycarbonylaminoethanol. The condensatione product is then dissolved in formic acid to remove the protecting group. Alternatively, 1,2-dilauroyl-sn-glycerol may be converted to 1,2-dilauroyl-sn-glycero-3-phosphoric acid dichloride by phosphorylation with phosphorus oxychloride in the presence of triethylamine, in molar ratios of diacylglycerol:phosphorus oxychloride:base, 1:1.5:1.5. The excess phosphorous oxychloride is removed by evaporation and the 1,2-dilauroyl-sn-glycero-3-phosphoric acid dichloride thus obtained is reacted with ethanolamine in the presence of triethylamine (molar ratios 1:1:2). The reaction is completed after 30 min and the intermediate 1,3,2-oxazaphospholane is recrystallized from hexane. Hydrolysis of the phospholane in 2-propanol in the presence of weak acids, e.g., formic or boric acids, results in the precipitation of the phosphatidylethanolamine.

The neutral phosphatidylethanolamines may be used with any of a variety of cationic lipids, in place of or in addition to other known helper lipid components, to form lipid carriers, which are useful as carriers for various biological molecules, such as nucleic acids. In particular, the lipids can be used in formulations for the preparation of lipid vesicles or liposomes for use in intracellular delivery systems. See Lasic, D., *Liposomes: From Physics to Applications*, Elsevier: Amsterdam, 1993. Uses contemplated for the lipids of the invention include both in vivo and in vitro transfection procedures corresponding to those presently known that use cationic lipid carriers, including those using commercial cationic lipid preparations, such as Lipofectin™, and various other published techniques using conventional cationic lipid technology and methods. See, generally, Lasic and Templeton (1996) Adv. Drug Deliv. Rev. 20: 221–266 and references cited therein. The lipid carriers of the invention can be used in pharmaceutical formulations to deliver therapeutic agents by various routes of administration, and to various sites in an animal body, to achieve a desired therapeutic effect. As an example, by substituting DLPE for cholesterol as the helper lipid for transfection by intravenous administration, transfection efficiency can be improved by approximately ten-fold.

Cationic lipids useful in combination with the neutral lipids of the invention include, for example, imidazolinium derivatives (WO 95/14380), guanidine derivatives (WO 95/14381), phosphatidyl choline derivatives (WO 95/35301), piperazine derivatives (WO 95/14651), and biguanide derivatives (as disclosed in co-owned and co-pending U.S. patent application Ser. No. 08/825,854, Attorney Docket No. 97,171). Examples of cationic lipids that may be used in the present invention include DOTIM (also called BODAI) (Solodin et al., (1995) Biochem. 34: 13537–13544), DDAB (Rose et al., (1991) BioTechniques 10(4):520–525), DOTMA (U.S. Pat. No. 5,550,289), DOTAP (Leventis and Silvius (1990) Biochim. Biophys. Acta 1023(1):124–132), DMRIE (Felgner et al., (1994) J. Biol. Chem. 269(4): 2550–2561), EDMPC (commercially available from Avanti Polar Lipids, Alabaster, Ala.), DC-Chol (Gau and Huang (1991) Biochem. Biophys. Res. Comm. 179:280–285, DOGS(Behr et al., (1989) Proc. Natl. Acad. Sci. USA, 86:6982–6986, MBOP (also called MeBOP or MBN222) (WO 95/14651), and those described in WO 97/00241. Particularly preferred are EDMPC for aerosolized delivery to airway epithelial cells and for intraperitoneal delivery, and DOTIM, DOTAP or MBN222 for intravenous delivery to vascular endothelial cells of various organs, especially the lung.

Compositions of the present invention will be usable in the manner described for other known neutral lipids, e.g., DOPE or cholesterol, in conjunction with the various cationic lipids, although optimization of operating parameters will improve results, using the specific information provided in this specification along with the knowledge of a person of skill in the art of lipid preparation and use. A reader unfamiliar with this background information is referred to the publications under the heading Relevant Literature above and further to PCT patent application numbers WO 96/40962 and WO 96/40963. These last-cited patent applications describe a number of therapeutic formulations and methods in detail, including examples of the use of specific cationic and neutral lipids that can be followed substantially be substituting, e.g., DLPE or DiPPE for the neutral lipids described.

The lipid carriers of the invention will generally be a mixture of cationic lipid and helper lipid in a molar ratio of from about 3:1 to 1:3, preferably about 1:1. The lipid carriers may include one or more cationic lipid, and may include DLPE or DiPPE alone as the helper lipid, or may include additional non-cationic helper lipids, which may be either anionic or neutral lipids. Usually, the lipid carriers will have as the lipid components a single cationic lipid and a single neutral lipid, preferably in approximately equimolar amounts.

The lipid mixtures typically are prepared in chloroform, dried, and rehydrated in, e.g., 5% dextrose in water or a physiologic buffer to form liposomes. Low ionic strength solutions are preferred. Liposomes may be LUVs, MLVs, or SUVs. Usually, the liposomes formed upon rehydration are predominantly MLVs, and SUVs are formed from them by sonication or by extrusion through membranes with pore sizes ranging from 50 to 600 nm to reduce their size. Most preferably, the liposomes are extruded through a series of membranes with decreasing pore sizes, e.g., 400 nm, 200 nm and 50 nm.

The resulting liposomes are mixed with a nucleic acid solution with constant agitation to form the cationic lipid-nucleic acid transfection complexes. The preferred size will vary depending on use. For example, smaller transfection complexes are preferred for aerosol administration, thereby reducing shear caused by the aerosolization process. Preferred transfection complex size for aerosol administration is less than 5000 nm, most preferably from 50 to 300 nm. Preferred transfection complex size for intravenous administration is from 50 to 5000 nm, most preferably from 100 to 400 nm.

Cationic lipid-nucleic acid transfection complexes can be prepared in various formulations depending on the target cells to be transfected. See, e.g., WO 96/40962 and WO 96/40963. DLPE or DIPPE may be substituted into a formulation in place of a different neutral lipid, and used in the same concentration, DNA-lipid ratio, etc. However, because substitution of the neutral lipid will result in changes in the physical characteristics of the lipid carrier, it is preferred that additional formulations be tested empirically to obtain optimal results. While a range of lipid-nucleic acid complex formulations will be effective in cell transfection, optimum conditions are determined empirically in the desired experimental system. Lipid carrier compositions may be evaluated by their ability to deliver a reporter gene (e.g. CAT which encodes chloramphenicol acetyltransferase, luciferase, or β-galactosidase) in vitro, or in vivo to a given tissue in an animal, such as a mouse.

For in vitro transfections, the various combinations are tested for their ability to transfect target cells using standard molecular biology techniques to determine DNA uptake, RNA and/or protein production. Typically, in vitro cell transfection involves mixing nucleic acid and lipid, in cell culture media, and allowing the lipid-nucleic acid transfection complexes to form for about 10 to 15 minutes at room temperature. The transfection complexes are added to the cells and incubated at 37° C. for about four hours. The complex-containing media is removed and replaced with fresh media, and the cells incubated for an additional 24 to 48 hours.

In vivo, particular cells can be preferentially transfected by the use of particular cationic lipids for preparation of the lipid carriers, for example, by the use of EDMPC to transfect airway epithelial cells (WO 96/40963) or by altering the cationic lipid-nucleic acid formulation to preferentially transfect the desired cell types (WO 96/40962). Thus, for example, in circumstances where a negatively charged complex is desired, relatively less cationic lipid will be complexed to the nucleic acid resulting in a higher nucleic acid: cationic lipid ratio. Conversely, in circumstances where a positively charged complex is desired, relatively more cationic lipid will be complexed with the nucleic acid, resulting in a lower nucleic acid: cationic lipid ratio. To avoid precipitation, which generally occurs around charge neutrality, net positively charged complexes are generally prepared by adding nucleic acid to the liposomes, and net negatively charged complexes are prepared by adding liposomes to the nucleic acid, in either case with constant agitation.

The lipid mixtures are complexed with DNA in different ratios depending on the target cell type, generally ranging from about 6:1 to 1:20 μg DNA:nmole cationic lipid. For transfection of airway epithelial cells, e.g., via aerosol, intratracheal or intranasal administration, net negatively charged complexes are preferred. Thus, preferred DNA:cationic lipid ratios are from about 10:1 to about 1:20, preferably about 3:1. For intravenous administration, preferred DNA:cationic lipid ratios range from about 1:3.5 to about 1:20 μg DNA: nmole cationic lipid, most preferably, about 1:6 to about 1:15 μg DNA: nmole cationic lipid. Additional parameters such as nucleic acid concentration, buffer type and concentration, etc., will have an effect on transfection efficiency, and can be optimized by routine experimentation by a person of ordinary skill in the art. Preferred conditions are described in the Examples that follow. For intraperitoneal delivery, particularly to peritoneal tumors, a preferred formulation consists of EDMPC and DiPPE in a 1:1 molar ratio, 1:8 DNA:cationic lipid ratio (μ DNA: nmole cationic lipid), 0.25 mg/ml DNA, in a 2.5 mM histidine buffer, pH 5.0 and 5% w/v dextrose.

Non-lipid material, (such as biological molecules being delivered to an animal or plant cell or target-specific moieties) can be conjugated to the lipid carriers through a linking group to one or more hydrophobic groups, e.g., using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains which will allow their association with the lipid mixture without covalent linking to one or more lipid groups.

For the most part, the active compounds to be bound to the lipid mixture are ligands or receptors capable of binding to a biological molecule of interest. For example, a ligand binding specifically to a receptor on a particular target cell type can be used to target delivery of the lipid carrier (with, e.g., the DNA or antibiotic of interest) to the desired target cells. Alternatively, the active compound may be a peptide or other small molecule designed to regulate intracellular trafficking of the delivered substance, e.g., triggering endosomal release or transport into the nucleus using a nuclear localizing sequence.

The active compounds bound to the lipid mixture can vary widely, from small haptens (molecular weights of about 125 to 2000) to antigens (molecular weights ranging from around 6000 to 1 million). Of particular interest are proteinaceous ligands that bind to and are internalized by specific complementary binding partners on cell surfaces. Illustrative active compounds include cytokines, interferons, hormones, antibodies to cell surface receptors or other molecules, and fragments of such compounds that retain the ability to bind to the same cell surface binding partners that bind the original (non-fragment) molecules.

The number of active compounds bound to a lipid carrier will vary with the size of the complex, the size of the compound, the binding affinity of the molecule to the target cell receptor or ligand, and the like. Usually, the bound active molecules will be present in the lipid mixture in from about 0.001 to 10 mole percent, more usually from about 0.01 to 5 mole percent based on the percent of bound molecules to the total number of molecules available in the mixture for binding.

The lipid carrier compositions are particularly useful as carriers for use in vivo, particularly in vivo in humans. Particularly where repeat administration is necessary or desirable, the carriers should be screened for toxicity. Choice of neutral lipid can modulate toxicities observed with cationic lipids in different formulations, and thus each combination should be tested separately. An animal, such as a mouse, can be administered one or more doses of material containing between 10nmole and 10μof the lipid to be tested, typically complexed with the intended active component (such as DNA). At various times after administration the animals are monitored for evidence of toxicity, e.g. lethargy or inflammation. The animals are sacrificed and the liver examined for toxicity. Total lipid may also be analyzed for the particular lipids or partial degradation products using, e.g., HPLC.

Delivery can be by any means known to persons of in the art, e.g., intravenous, intraperitoneal, intratracheal, intranasal, intramuscular, intradermal, etc. PCT patent application WO 96/40962 describes the preparation and use of cationic lipid carriers for in vivo DNA delivery. For aerosol administration, via intranasal or intraoral delivery, the cationic lipid-nucleic acid transfection complex will withstand both the forces of nebulization and the environment within the lung airways and be capable of transfecting lung cells. Techniques for delivering genes via aerosol administration of cationic lipid-DNA transfection complexes is described in PCT patent application WO 93/12756.

The various lipid-nucleic acid complexes are prepared by known methods, for example, as described in PCT application number WO 95/14381 and WO 96/40962. Precipitation of resultant lipid-DNA mixtures is determined by visual inspection. While precipitation does not preclude the use of such complexes for in vitro transfection purposes, precipitated complexes are not desirable for in vivo transfection. To make the lipid-DNA complexes more visible, the complexes can be stained with a dye that does not itself cause aggregation, but which will stain either the DNA or the lipid. For example, Sudan black (which stains lipid) can be used as an aid to examine the lipid-DNA mixture to determine if aggregation has occurred. Particle size can be studied by methods known in the art including, for example, electron microscopy, laser light scattering, Coulter™ counting/sizing, and the like. Standard-size beads can be used for calibration to determine the size of liposomes or complexes that form.

The following examples are offered by way of illustration and not by way of limitation.

EXAMPLES

Example 1

Screening of Neutral Lipids for IV Gene Delivery

Nine compounds, the structures of which are shown in FIG. 1, were tested for their ability to mediate transfection when incorporated as the neutral lipid into cationic liposomes. One of the compounds was DOPE, which is a commonly used neutral lipid. All compounds tested were phosphatidyl ethanolamine derivatives, which varied in chain length, saturation, and extent of branching. The different neutral lipids were tested in combination with the cationic lipid BODAI (also known as DOTIM) or DOTAP. As controls BODAI and DOTAP were also used with cholesterol as the neutral lipid, which combinations were know to give high transfection efficiencies in vivo.

The lipid combinations were tested as carriers for gene transfer by intravenous delivery in ICR female mice (25 g), and expression was determined using the plasmid p4119 containing the CAT reporter gene under the control of the HCMV promoter. The lipids were dissolved in a mixture of chloroform and methanol (1:1). Lipid films of cationic and neutral lipid at a 1:1 molar ratio were formed with a rotary evaporator. The films were hydrated with 5% dextrose in water (D5W) at room temperature and extruded through a series of membranes having pore sizes of 400 nm, 200 nm, and 50 nm.

DNA-liposome complexes were prepared at a 1:10 DNA-:cationic lipid ratio (mg DNA:$\mu$mole cationic lipid) by adding the DNA, in a solution at 0.625 mg/ml concentration in D5W to the solution of liposomes, in an equal volume, with constant stirring, using a Hamilton Dilutor 540B (Hamilton, Reno, Nev.). BODAI:cholesterol was used at a 1:6 DNA:cationic lipid ratio. The DNA solution was 0.3125 mg/ml DNA in D5W. The resulting complexes were sized using a Submicron Particle Sizer 370 (Nicomp, Santa Barbara, Calif.). Zeta potential was determined by a Zeta Plus, Zeta Potential Analyzer (Brookhaven Instruments Corp.).

A total of 5 mice were tested per group. A dose of 62.5 $\mu$g p4119 plasmid DNA in 200 $\mu$l D5W was injected by tail vein per mouse. The lung, heart, liver, and spleen were harvested after 24 h and assayed for CAT activity. Each organ was homogenized in 1.0 m of 5 mM EDTA/0.25M Tris-HCl pH 7.8 containing 5 $\mu$g/ml Aprotinin (Boehringer Mannheim, Indianapolis, Ind.), 5 $\mu$g/ml Leupeptin (Boehringer Mannheim, Indianapolis, Ind.), and 5 mM PMSF (Boehringer Mannheim, Indianapolis, Ind.), The resulting extracts were centrifuged and aliquots of the supernatant were removed for protein analysis, utilizing a bicinchoninic acid based reagent kit (Pierce, Rockford, Ill.). The remaining supernatant was heat treated at 65° C. for 15 min. The CAT activity assay was performed using 5 ul of heat treated supernatant, 25 ul of 125 ug/ml n-Butyryl CoA (Sigma, St. Louis, Mo.), 50 ul of 5uCi/ml 14C-chloramphenicol (DuPont NEN, Boston, Mass.), and 50 ul of 0.25M Tris-HCl/5 mM EDTA. Samples were incubated at 37° C. for 2 h. An addition of 300 ul of mixed xylenes (Aldrich, Milwaukee, Wis.) was made followed by vortexing and centrifugation at 14 K rpm for 5 min. The xylene layer was then transferred into 750 $\mu$l of 0.25 M Tris-HCl/5mM EDTA, vortexed, and centrifuged at 14 K rpm for 5 min. The upper organic phase was then transferred into scintillation vials containing 5 ml of Ready Safe Liquid Scintillation Cocktail (Beckman, Fullerton, Calif.). Samples were counted for 1 min each.

Figure 2:
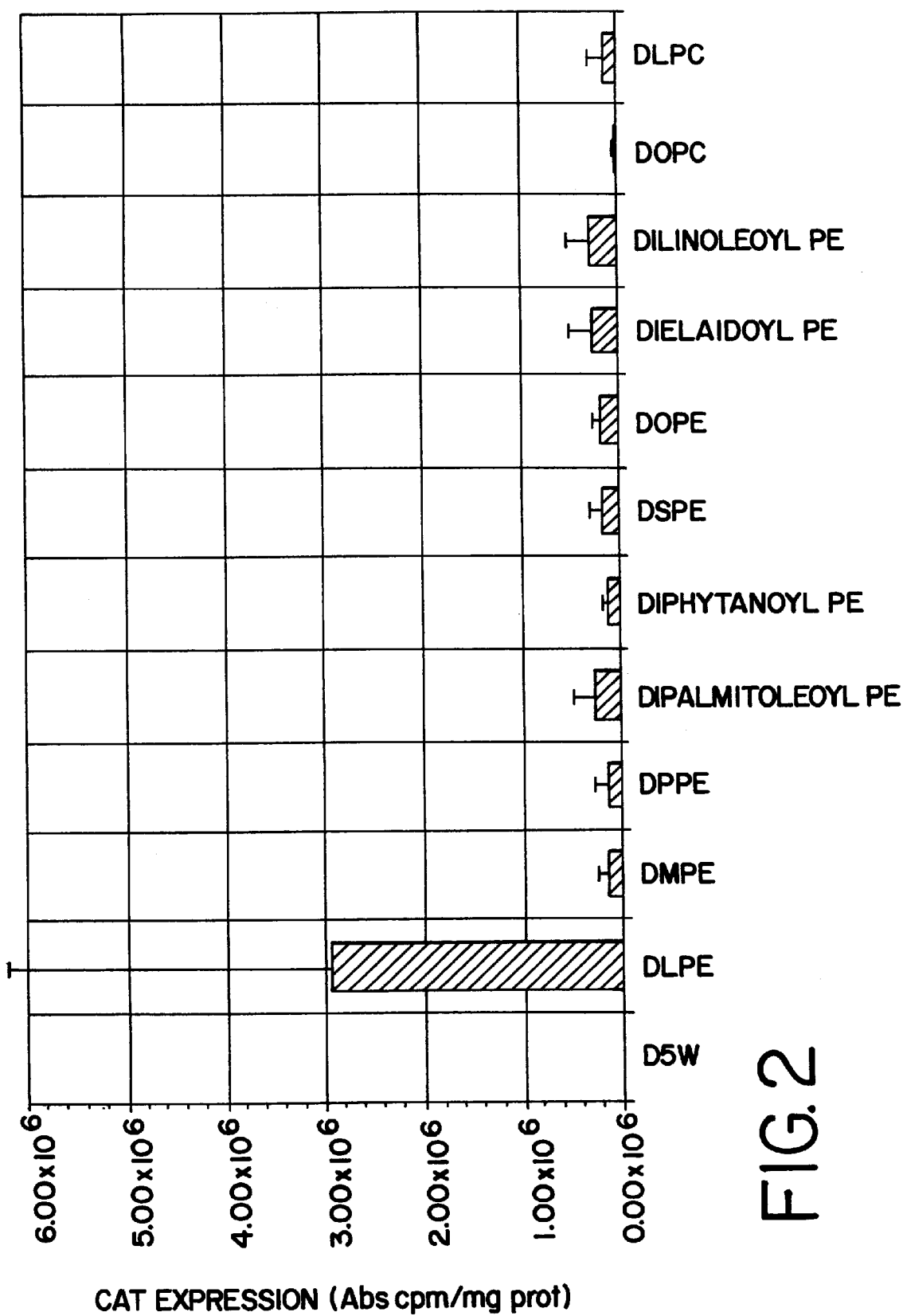
FIG. 2 is a histogram showing the levels of transfection obtained in lung tissue, as measured by CAT expression, resulting from transfection of a CAT reporter plasmid using various lipid formulations as described in Example 1.
Figure 3:
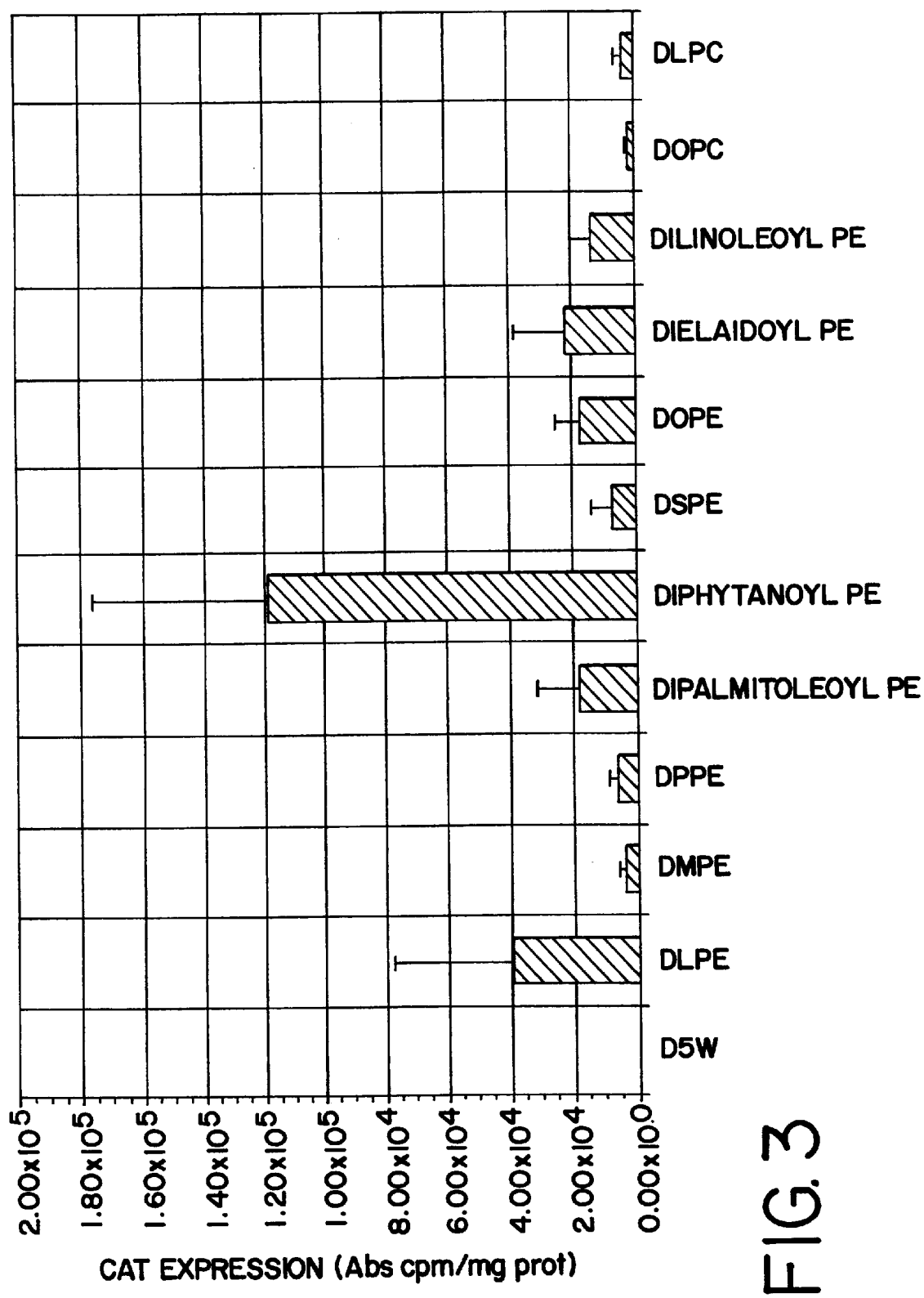
FIG. 3 is a histogram showing the levels of transfection obtained in spleen tissue, as measured by CAT expression, resulting from transfection of a CAT reporter plasmid using various lipid formulations as described in Example 1. This Figure includes a comparison of helper lipids with BODAI in transgene expression in spleen following I.V. administration.
Figure 4:
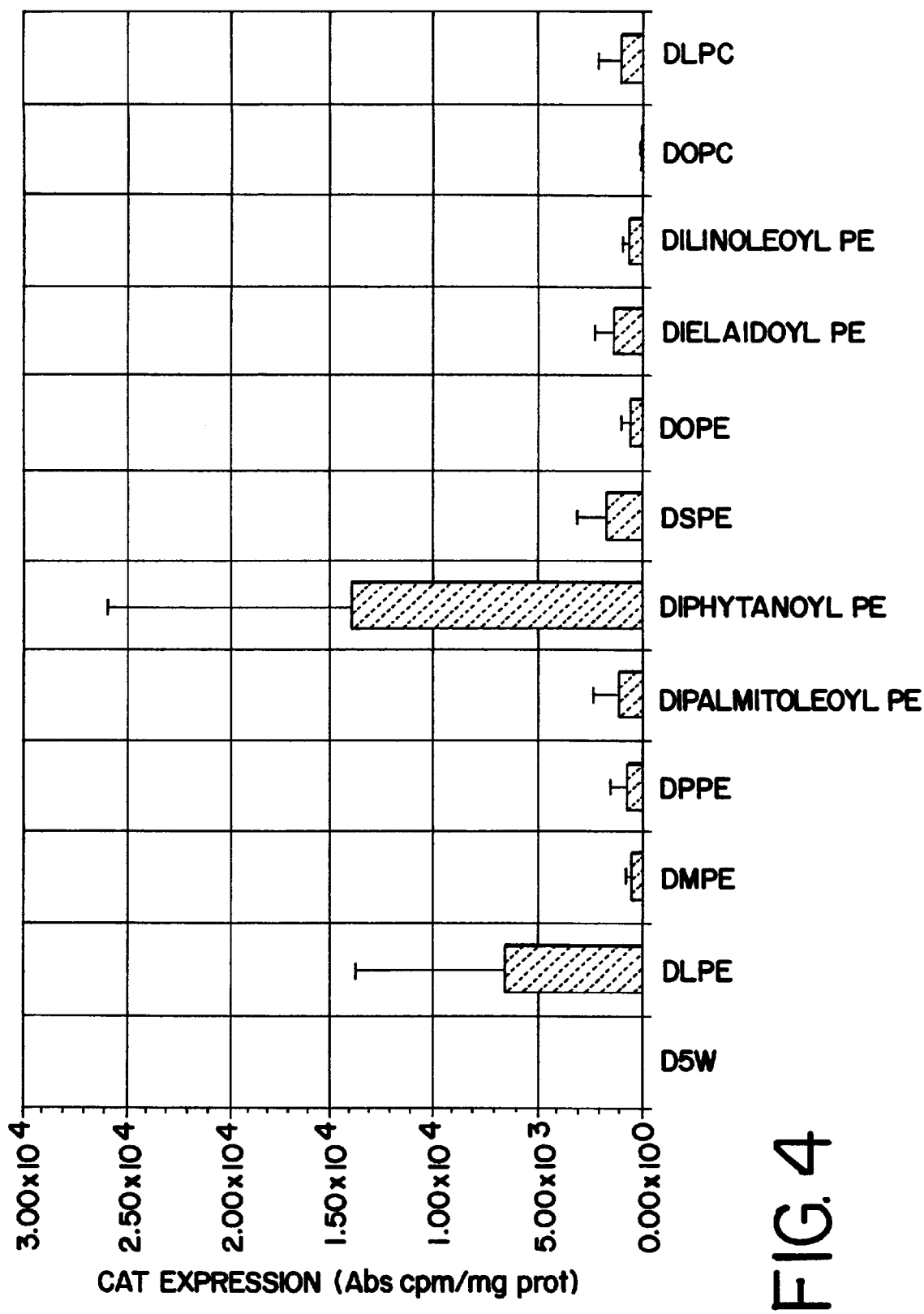
FIG. 4 is a histogram showing the levels of transfection obtained in liver tissue, as measured by CAT expression, resulting from transfection of a CAT reporter plasmid using various lipid formulations as described in Example 1. This Figure includes a comparison of helper lipids with BODAI in transgene expression in liver following I.V. administration.
Figure 5:
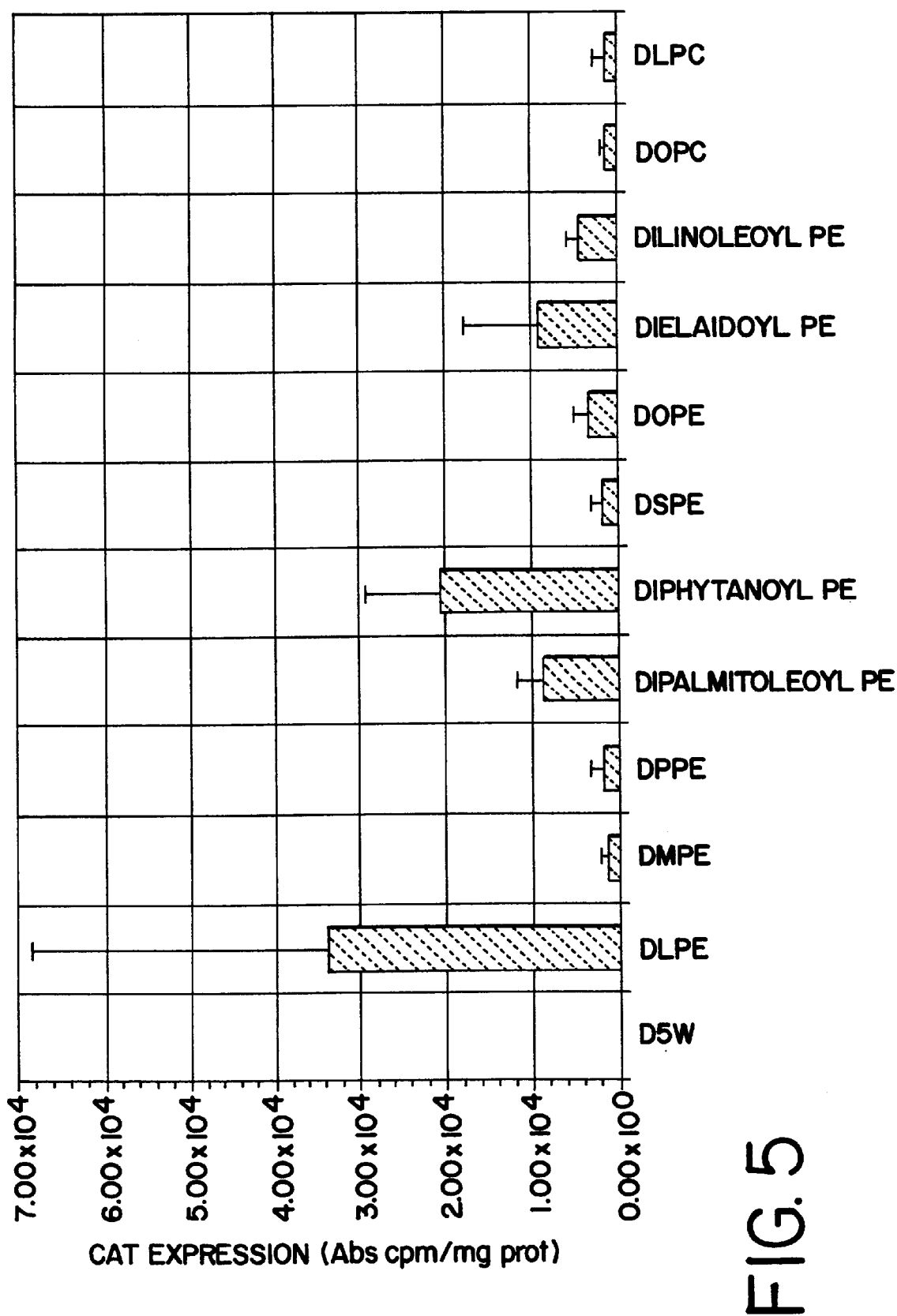
FIG. 5 is a histogram showing the levels of transfection obtained in heart tissue, as measured by CAT expression, resulting from transfection of a CAT reporter plasmid using various lipid formulations as described in Example 1. This Figure includes a comparison of helper lipids with BODAI in transgene expression in heart following I.V. administration.

FIG. 2 shows resulting expression levels in the lung; FIG. 3 shows expression in the spleen; FIG. 4 shows expression in the liver; and FIG. 5 shows expression in the heart. The results show that in the lung, only formulations using either cholesterol (not shown) or DLPE as the neutral lipid showed significant expression levels. All other neutral lipids tested, including DOPE, showed very low expression levels in the lung. In the other organs tested, DLPE and cholesterol (not shown) also showed significant expression levels. In the liver, spleen and heart, diphytanoyl phosphatidylethanolamine also showed high expression levels. It is likely that expression detected in the lung is due to transfection of vascular endothelial cells, and in the spleen and liver, and to a lesser extent the heart, expression is due to transfection of macrophages. This suggests that diphytanoyl phosphatidylethanolamine mediates high transfection levels of macrophages as compared to vascular endothelial cells.

Example 2

Comparison of Neutral Lipids with Different Cationic Lipids

Transfection efficiencies using DLPE as the neutral lipid were compared to those obtained using cholesterol as the neutral lipid, each in combination with various cationic lipids. The cationic lipids used were BODAI, DOTAP, MBN222 (also called MBOP or MeBOP), MBN231 (1MBG, disclosed in co-owned and co-pending U.S. patent application Ser. No. 08/825,854, Attorney Docket No. 97,171) and MBN233 (DOBG, disclosed in co-owned and co-pending U.S. patent application Ser. No. 08/825,854, Attorney Docket No. 97,171). The formulations were tested at the DNA:cationic lipid ratios shown in Table 1. In all cases, BODAI:cholesterol, 1:6 $\mu$g DNA: nmole cationic lipid ratio was used as a positive control. For each protocol, the transfection efficiency is expressed as relative activity compared to the BODAI:cholesterol control.

Complexes were prepared and animals dosed as described in Example 2. Transfection was determined by measuring CAT activity as described in Example 2, or by measuring the amount of CAT protein by ELISA (expressed as pg CAT/mg protein). The ELISA assay was performed by first harvesting the lung, heart, liver and spleen 24 hr after injection. Each organ was homogenized in 1 ml of 5 mM EDTA/0.25M Tris-HCl pH 7.8 containing 5 $\mu$g/ml Aprotinin (Boebringer Mannheim, Indianapolis, Ind.), 5 $\mu$g/ml Leupeptin (Boehringer Mannheim), and 5 mM PMSF (Boehringer Mannheim). The resulting extracts were centrifuged and aliquots of the supernatant were removed for protein analysis, utilizing a bicinchoninic acid-based reagent kit (Pierce, Rockford, Ill.). Each well of a Corning EIA/RIA 96-well plate was coated overnight at 4–8° C. with 0.6 $\mu$g rabbit anti-CAT antibody (5 Prime-3 Prime, Boulder, Colo.) diluted in 50 $\mu$l of 50 mM sodium bicarbonate buffer (pH 9.5). The coated plate was incubated at room temperature for one hour with 200 $\mu$l PBS pH 7.4 containing 5% (w/v) non-fat dry milk and 0.2% (v/v) Tween-20 (Blotto) to block non-specific binding sites. The plates were washed four times in 0.2% Tween-20 in PBS, and incubated for 1 hr at 37° C. with 50 $\mu$l sample (in 1:2 serial dilutions). The plates were washed four times in wash buffer, and incubated 45 min at 37° C. in 50 $\mu$l Digoxigenin labeled sheep anti-CAT antibody (Boehringer Mannheim) (1:100 in Blotto). Plates were washed again and incubated 45 min at 37° C. in 50 $\mu$l peroxidase-conjugated Fab fragment of sheep anti-DIG antibody (Boehringer Mannheim) (1:400 in Blotto). Plates were washed again and the color reaction developed in 150 $\mu$l 5 mg/ml ABTS in 0.1 M citrate buffer (pH 4.2) containing 0.3% hydrogen peroxide. Color changes were read on a SPECTRAmax™ 250 using Softmax Pro V.1.2 software (Molecular Devices, Sunnyvale, Calif.) at A405–A490. Results were calculated based on a standard curve generated by 1:2 serial dilutions of known CAT enzyme (Boehringer Mannheim).

The results shown in Table 1 show that improved transfection efficiencies were obtained with DLPE as the neutral lipid as compared to cholesterol, for all the cationic lipids tested (with the exception of spleen transfection using MBN233). The improvement in expression was up to 12-fold.

Table 2 is a summary of transfections performed using DLPE as the neutral lipid, and shows comparisons of different cationic lipids and different DNA: cationic lipid ratios. Again, relative activity represents the ratio of transfection activity compared to the BODAI:cholesterol (1:6) positive control. High transfection rates were obtained with all cationic lipids tested, with best results obtained at DNA:cationic lipid ratios in the 1:7.5 to 1:10 range.

Example 3

Effect of Neutral Lipid on DNA Uptake and Intracellular Trafficking

1. Cells

Cell lines were cultured in media from GIBCO, BRL (Gaithersburg, Md.); along with additional supplements needed for optimal growth. C57 MG cells grew in DMEM supplemented with 10% fetal bovine serum, and 2 mM L-glutamine. CHO-K1 (ATCC CCL-61) cells' growth media consisted of F12 media supplemented with 10% fetal bovine serum. COS-1 (ATCC CRL-1650) cells were grown in DMEM/F12 media supplemented with 10% fetal bovine serum, and 2 mM L-glutamine.

2. Transfection

Equimolar solutions of BODAI and the appropriate helper lipid (both in chloroform) were mixed in 100 ml round bottom flasks. Following evaporation of the chloroform using a Buchi rotary evaporator, 5% w/v dextrose was used to rehydrate the lipid film to a final concentration of 20 mM based on input lipid. Liposome formation was achieved by extrusion through a 0.2 $\mu$ filter (5x) followed by extrusion through a 0.05 $\mu$ filter (11x). The liposome solution was finally filtered through a 0.22 $\mu$filter under sterile conditions prior to storage at 4° C.

Complexing was performed by mixing 100 $\mu$l of a 0.625 mg/ml solution of the plasmid of interest (CAT, GFP or Rhodamine labeled plasmid) with an equal volume of the cationic liposome formulations at ratios of 1:15, 1:10, 1:6, 1:1 and 3:1 (mg DNA/ $\mu$mol cationic lipid) for a final concentration of 0.3125 mg DNA/ ml complex. If the final net charge of the complex was positive, the appropriate volume of DNA was added to the liposome; the reverse order was employed if the final net charge of the complex was negative. Immediately after this addition, the mixture was rapidly hand pipetted ~10 times up and down with a micropipet.

Twenty-four hours prior to transfection, 200,000 cells were seeded per well in 6-well dishes from Costar Corporation (Cambridge, Mass.). After changing the cells' growth media immediately prior to the transfection, 5 $\mu$l of the complexes (~1.5 $\mu$g DNA) was added to each well and rocked gently from side-to-side to thoroughly disperse the added complex. Four hours after transfection the cells' growth media was replaced, and the cells were incubated at 37° C. Triplicate wells were transfected for each condition from which the mean and standard deviation were calculated.

3. Cell Harvest

GFP and Uptake Assays

Approximately 24 hours after transfection, cells were harvested by gently washing the wells with 2 ml 1x PBS, followed by the addition of 200 $\mu$l of 0.25% trypsin in 1 mM EDTA (GIBCO, BRL; Gaithersburg, Md.). After collecting the liberated cells by the addition of 1 ml serum-containing media, cells were centrifuged at 4,000 rpm for 6 minutes at 4° C.

Cell pellets were resuspended in 400 $\mu$l of FACS buffer (5% FBS, 0.1 mM EDTA, 5 $\mu$g/ml propidium iodide (used in GFP assay only) in PBS) and filtered through a 35 $\mu$m strainer into tubes appropriate for sampling on the FACscan instrument (see below) (Falcon; 12x75 mm polystyrene; VWR Scientific; Pittsburgh, Pa.).

CAT Assay

Approximately 24 hours after transfection, cells were gently washed twice with 2 ml 1x PBS. Immediately following the wash, cells were lysed by adding 1 ml of 1 x passive cell lysis buffer (Promega Corporation; Madison, Wis.) per well and incubated at 4° C. for a maximum of 30 minutes. Cells were scraped off the wells, using a pipette tip in a constant circular motion, followed by the immediate incubation of the cell solutions on ice. A brief (·2 seconds) vortexing of the microtubes containing the cells was followed by centrifugation at 10,000 rpm for 10 minutes at 4° C. 800 $\mu$l of the cell lysate (supernatant) was collected and stored them at –70° C. for CAT analysis. 4. Data Acquisition and Analysis GFP Assay 10,000 events were acquired on the FACscan via the LYSYS II software package (Becton Dickinson). Forward angle scatter and side angle scatter gating in conjunction with PI gating delineated the viable cell population. The analysis marker region indicating positive GFP expression (measured on the FL1 channel) was set based on mock transfected cells (negative control plasmid formulated at each complex ratio) such that $\leq$1% of fluorescence from the appropriate mock sample was in the positive marker region. We performed all quantitative analyses using the WINMDI program (ver. 2.5, build 20; Windows Multiple Document Interface for Flow Cytometry, shareware; Joe Trotter, The Scripps Research Institute).

Uptake Assay 10,000 events were acquired on the FACscan via the LYSYS II software package (Becton Dickinson). Forward angle scatter and side angle scatter gating delineated the cell population. Rhodamine fluorescence was collected on the FL2 channel. The relative fluorescence for each transfection was calculated by dividing the mean fluorescence of the test population by the mean fluorescence of the mock transfected cells (negative control plasmid formulated at each complex ratio). We performed all quantitative analyses using the WINMDI program as above.

CAT Assay

Figure 6:
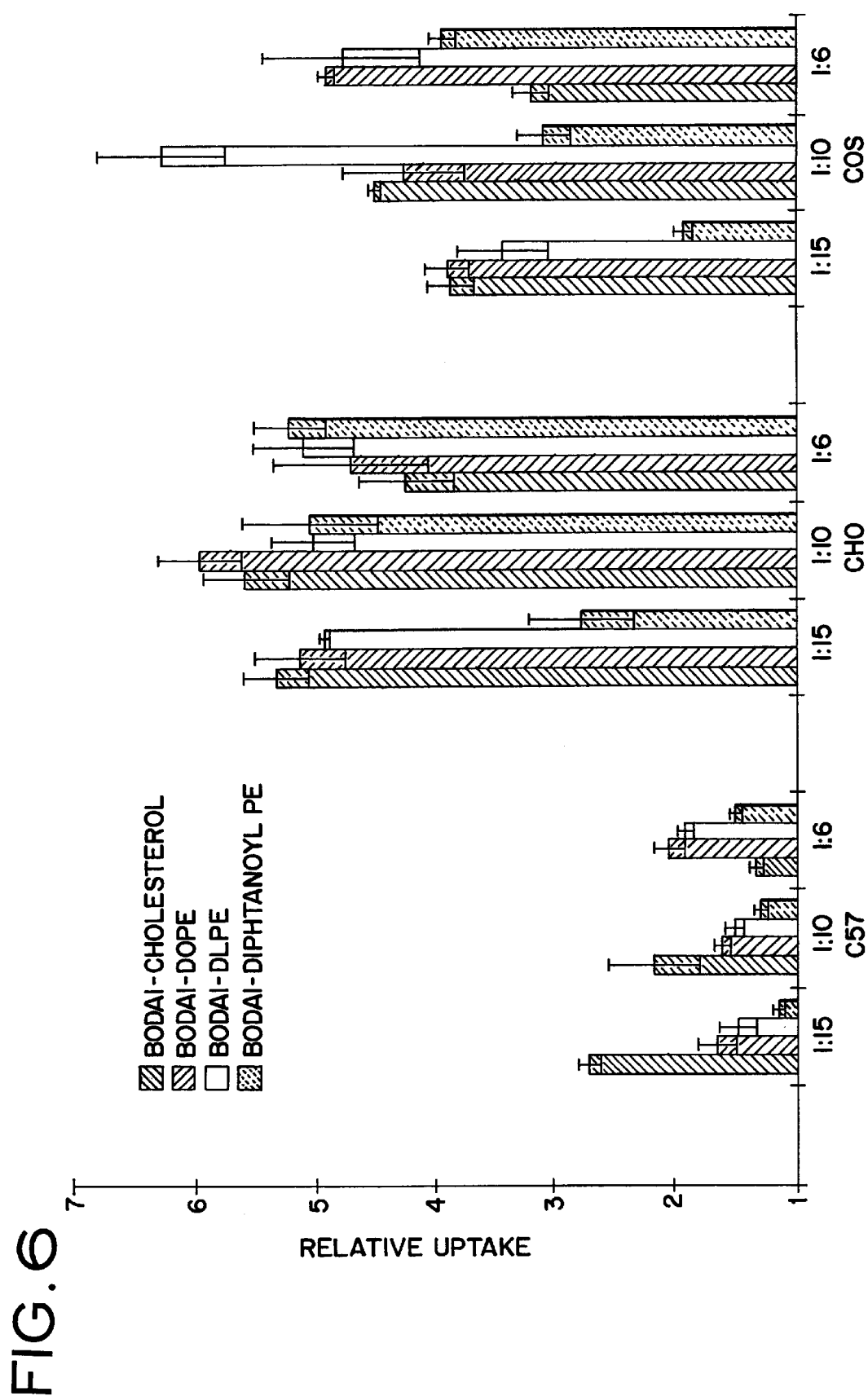
FIG. 6 is a histogram showing the DNA uptake with lipid/DNA complexes prepared with different neutral lipids, at varying lipid/DNA ratios, in C57, CHO and COS cells.

The supernatants containing the soluble protein fraction were transferred to storage tubes and stored at –70° C. until assayed. The total protein concentration of each sample was determined using a BCA microplate assay and BSA protein concentration standards (BCA Reagent and BSA standard: Pierce, Rockford, Ill.). The concentration of CAT protein in each sample was determined by analysis in a CAT-specific ELISA with a quantitation range between 15.6 and 250 pg/ml. CAT protein values are reported as ng of CAT enzyme per mg of total protein in the sample Results FIG. 6 shows the levels of DNA uptake by C57, CHO and COS cells of DNA/lipid complexes containing BODAI and one of cholesterol, DOPE, DLPE or DiPPE as the neutral lipid, at ratios of 1:15, 1:10 and 1:6. Under all conditions tested, C57 cells did not take up DNA as well as CHO or COS cells. In most cases there is not much difference between the neutral lipids with respect to DNA uptake, with the exception that BODAI/DiPPE uptake appears very low at the higher lipid/DNA ratios. One caveat to these results is that the procedure may not completely distinguish between complex association with the cell and actual cellular uptake.

Figure 7:
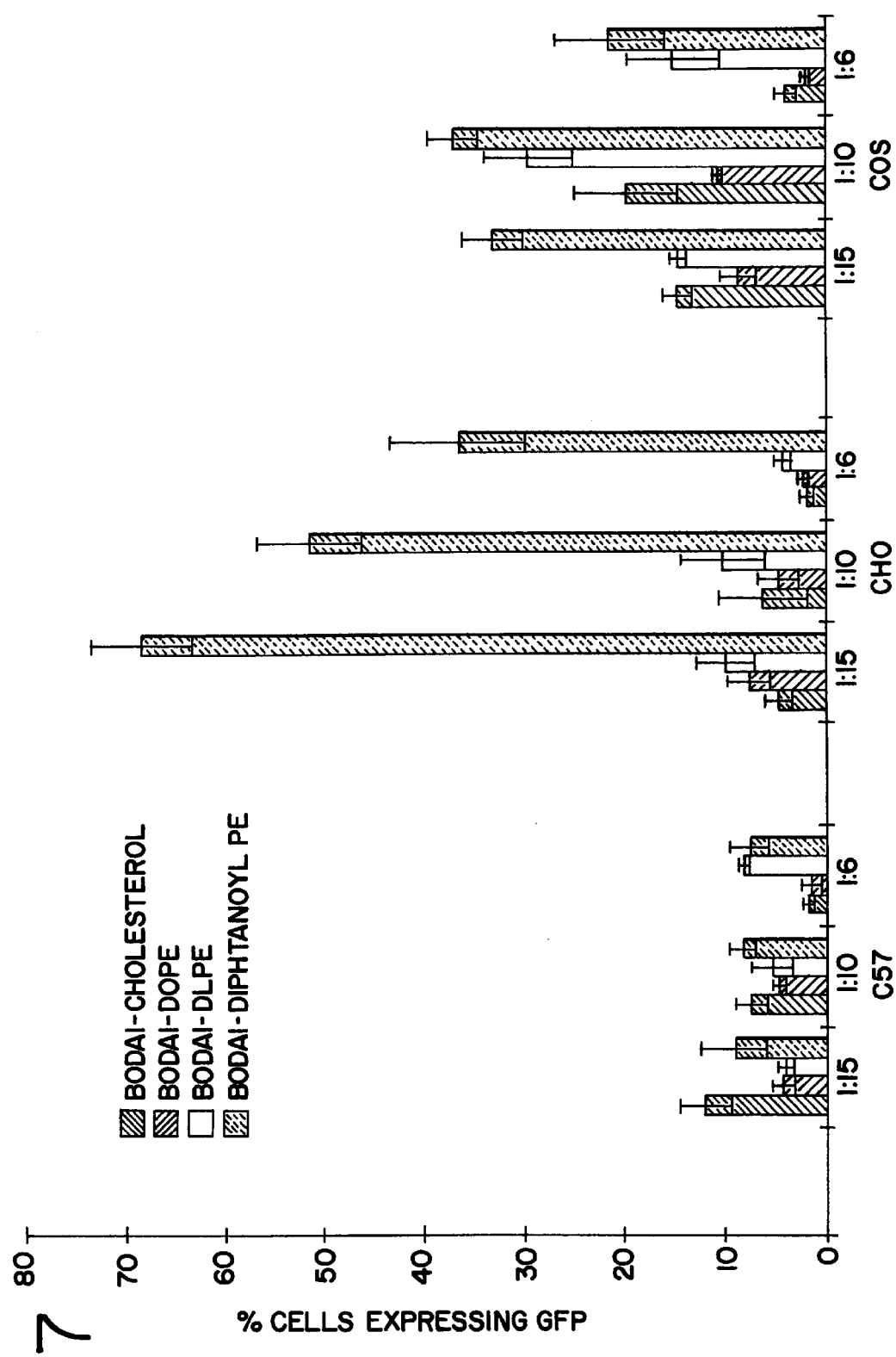
FIG. 7 is a histogram showing levels of GFP expression with lipid/DNA complexes prepared with different neutral lipids, at varying lipid/DNA ratios, in C57, CHO and COS cells.
Figure 8:
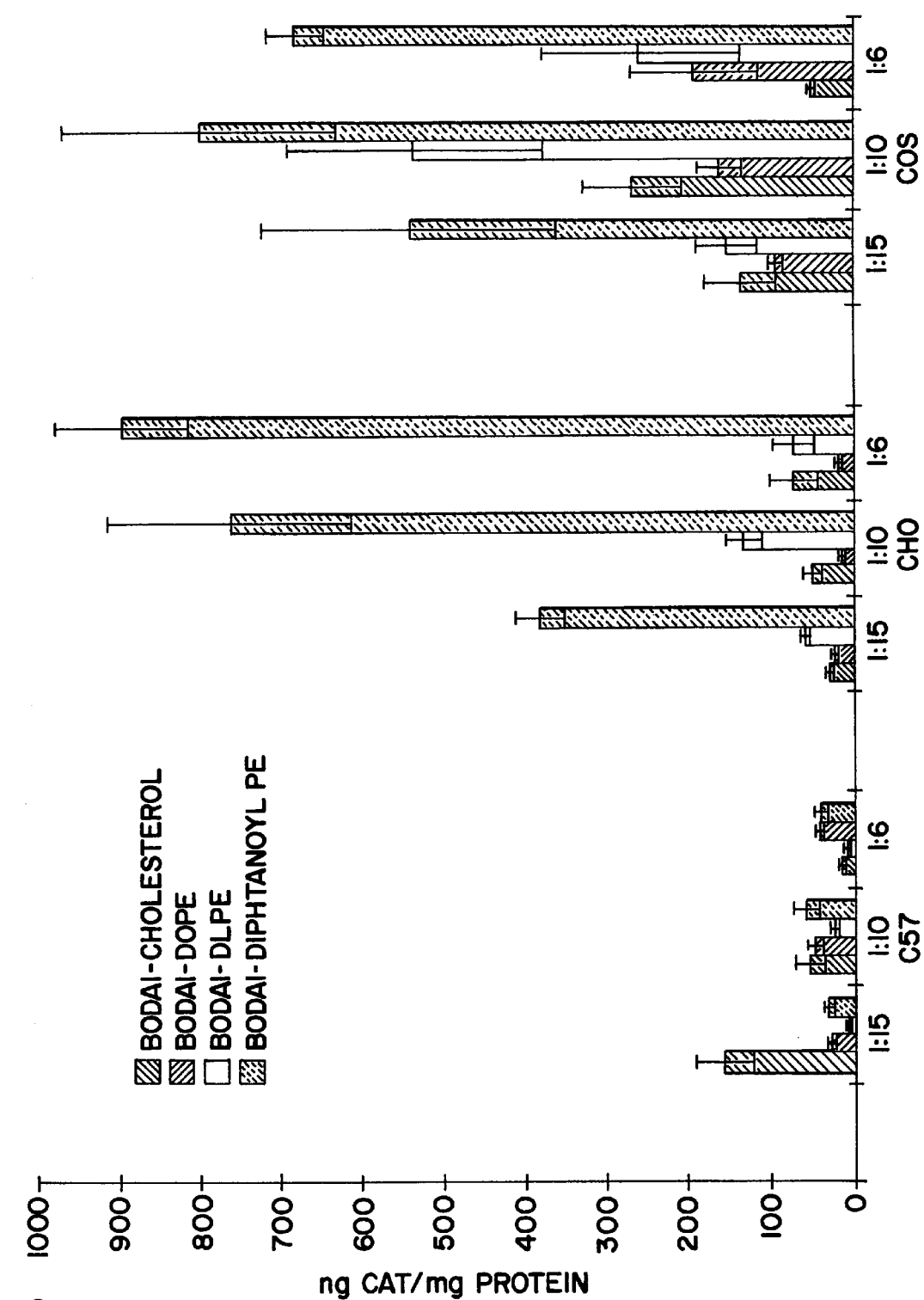
FIG. 8 is a histogram showing levels of CAT expression with lipid/DNA complexes prepared with different neutral lipids, at varying lipid/DNA ratios, in C57, CHO and COS cells.

FIGS. 7 and 8 show GFP and CAT expression, respectively, with the same DNA/lipid formulations. Surprisingly, both GFP and CAT expression are significantly higher with formulations containing DiPPE. The effect was most pronounced in CHO cells, but was also seen in COS cells. In COS cells, the DLPE-containing formulations also expressed at high levels in the 1:6 and 1:10 ratios. In C57 cells, expression is similar among the different formulations although the DiPPE-containing formulations were generally taken up to a lesser extent. Further FACS analysis of CHO cells transfected with 1:15 BODAI:cholesterol and BODAI:DiPPE formulations confirm that, on the cellular level, the DiPPE-containing formulation leads to less uptake and higher GFP expression, whereas the cholesterol-containing formulation leads to high uptake with considerably fewer cells expressing GFP (data not shown).

Taken together, these results suggest that, as a neutral lipid in cationic lipid-DNA formulations, DiPPE allows improved intracellular processing of the complexes after uptake. The improved expression with DiPPE-containing formulations may be due to improved endosomal release, improved nuclear transport, and/or an improved rate of decomplexation from the DNA within the cell.

All publications and patent applications cited herein are hereby incorporated by reference to the same extent as if fully set forth herein.

The invention now being fully described, it will be apparent to one of ordinary skill in the art that many changes and modifications can be made thereto without departing from the spirit or scope of the appended claims.

TABLE 1

Comparison of Neutral Lipid DLPE with Cholesterol

| Protocol No. | Liposome Formulations (molar ratio) | DNA/Cationic lipid (mg/ml:mM) | Lung Relative Activity | Lung New/Positive Control | Heart Relative Activity | Heart New/Control | spleen Relative Activity | spleen New/Control | liver Relative Activity | liver New/Control |
|---|---|---|---|---|---|---|---|---|---|---|
| MBIV-015-96 | Bodai/DLPE (1:1) | 1:10 | 5.72 | 5881/ 1029 | — | — | — | — | — | — |
| MBIV-015-96 | Bodai/Chol (1:1) | 1:6 | 1 | 1029/ 1029 | — | — | — | — | — | — |
| OM-064-96 | Bodai/DLPE (1:1) | 1:10 | 11.9 | 34,788,631/ 2,912,706 | — | — | — | — | — | — |
| OM-064-96 | Bodai/Chol (1:1) | 1:6 | 1 | 2,912,706/ 2,912,706 | — | — | — | — | — | — |
| OM-064-96 | DOTAP/DLPE (1:1) | 1:10 | 7.74 | 22,532,011/ 2,912,706 | — | — | — | — | — | — |
| OM-064-96 | DOTAP/Chol (1:1) | 1:10 | 0.39 | 1,103,544/ 2,912,706 | — | — | — | — | — | — |
| OM-079-96 | MBN-222/DLPE (1:1) | 1:7.5 | 7.73 | 36,099,982/ 4,669,638 | — | / 106668 | — | / 108648 | — | / 26110 |
| OM-079-96 | MBN-222/Chol (1:1) | 1:7.5 | 0.58 | 2,726,132/ 4,669,638 | — | / 20,371 | — | / 10,290 | — | / 4,435 |
| OM-090-96 | Bodai/DLPE (1:1) | 1:10 | 2.59 | 6,642,412/ 2,569,333 | 1.31 | 22,316/ 17,000 | 2.0 | 45,415/ 22,634 | 1.30 | 8,271/ 6,386 |
| OM-090-96 | Bodai/Chol (1:1) | 1:6 | 1 | 2,569,333/ 2,569,333 | 1 | 17,000/ 17,000 | 1 | 22,634/ 22,634 | 1 | 6,386/ 6,386 |
| OM-090-96 | MBN-231/DLPE (1:1) | 1:10 | 6.02 | 15,467,874/ 2,569,333 | 12.6 | 215,313/ 17,000 | 5.37 | 121,496/ 22,634 | 26 | 166,694/ 6,386 |
| OM-090-96 | MBN-231/Chol (1:1) | 1:10 | 1.06 | 2,734,917/ 2,569,333 | 6.53 | 111,090/ 17,000 | 1.22 | 27,563/ 22,634 | 2.76 | 17,637/ 6,386 |
| OM-090-96 | MBN-233/DLPE (1:1) | 1:10 | 4.48 | 11,518,150/ 2,569,333 | 4.41 | 74,919/ 17,000 | 12.0 | 272,586/ 22,634 | 14.0 | 89,218/ 6,386 |
| OM-090-96 | MBN-233/Chol (1:1) | 1:10 | 3.42 | 8,797,728/ 2,569,333 | 16.4 | 278,240/ 17,000 | 17.9 | 404,131/ 22,634 | 12.6 | 80,349/ 6,386 |

*Mean Cat Activity (cpm/mg protein) was for OM - protocols, and mean Elisa Activity (pg/mg protein) was for MBIV - protocols. The positive control was Bodai/Chol (1:1). The relative activity is the ratio of the transfection efficiency of new formulation to the positive control.

TABLE 2

Summary of Neutral Lipid DLPE

| | | | Transfection Efficiency* | | | | | | | |
|---|---|---|---|---|---|---|---|---|---|---|
| | Liposome | DNA/Cationic | Lung | | Heart | | spleen | | liver | |
| Protocol No. | Formulations (molar ratio) | lipid (mg/ml:mM) | Relative Activity | New/Positive Control | Relative Activity | New/ Control | Relative Activity | New/ Control | Relative Activity | New/ Control |
| OM-022-96 | Bodai/DLPE (1:1) | 1:6 | 0.45 | 1,981,020/ 4,371,208 | 0.22 | 8,639/ 39,449 | 0.63 | 26,708/ 42,095 | 2.15 | 4,868/ 2,261 |
| MBIV-015-96 | Bodai/DLPE (1:1) | 1:10 | 5.72 | 5881/ 1029 | — | — | — | — | — | — |
| OM-064-96 | Bodai/DLPE (1:1) | 1:10 | 11.9 | 34,788,631/ 2,912,706 | — | — | — | — | — | — |
| OM-064-96 | DOTAP/DLPE (1:1) | 1:10 | 7.74 | 22,532,011/ 2,912,706 | — | — | — | — | — | — |
| OM-067-96 | MBN-220/DLPE (1:1) | 1:7.6 | 0.0044 | 4,556/ 1,026,067 | — | — | 0.54 | 4,092/ 7,578 | — | — |
| MBIV-023-96 | MBN-222/DLPE (1:1) | 1:10 | 17.9 | 6884/ 384 | 16.6 | 65/ 3.9 | 4.1 | 66/ 16 | 5 | 15/ 3.1 |
| MBIV-023-96 | MBN-223/DLPE (1:1) | 1:10 | 0.27 | 104/ 384 | 7.1 | 27.8/ 3.9 | 3.0 | 47.9/ 16 | 4.4 | 13.8/ 3.1 |
| OM-079-96 | MBN-222/DLPE (1:1) | 1:3 | 0.0025 | 11,639/ 4,669,638 | — | — | — | — | — | — |
| OM-079-96 | MBN-222/DLPE (1:1) | 1:5 | 0.019 | 89,339/ 4,669,638 | — | / 7937 | — | / 17618 | — | / 4528 |
| OM-079-96 | MBN-222/DLPE (1:1) | 1:7.5 | 7.73 | 36,099,982/ 4,669,638 | — | / 106668 | — | / 108648 | — | / 26110 |
| OM-079-96 | MBN-222/DLPE (1:1) | 1:10 | 6.28 | 29,322,216/ 4,669,638 | — | / 78753 | — | / 44940 | — | / 11616 |
| OM-090-96 | Bodai/DLPE (1:1) | 1:10 | 2.59 | 6,642,412/ 2,569,333 | 1.31 | 22,316/ 17,000 | 2.0 | 45,415/ 22,634 | 1.30 | 8,271/ 6,386 |
| OM-090-96 | MBN-222/DLPE (1:1) | 1:5 | 0.62 | 1,598,464/ 2,569,333 | 1.39 | 23,595/ 17,000 | 3.38 | 76,399/ 22,634 | 5.93 | 37,866/ 6,386 |
| OM-090-96 | MBN-231/DLPE (1:1) | 1:10 | 6.02 | 15,467,874/ 2,569,333 | 12.6 | 215,313/ 17,000 | 5.37 | 121,496/ 22,634 | 26 | 166,694/ 6,386 |
| OM-090-96 | MBN-233/DLPE (1:1) | 1:10 | 4.48 | 11,518,150/ 2,569,333 | 4.41 | 74,919/ 17,000 | 12.0 | 272,586/ 22,634 | 14.0 | 89,218/ 6,386 |

*Mean Cat Activity (cpm/mg protein) was for OM - protocols, and mean Elisa Activity (pg/mg protein) was for MBIV - protocols. The positive control was Bodai/Chol (1:1). The relative activity is the ratio of the transfection efficiency of new formulation to the positive control.

We claim:

1. A lipid complex comprising a polyanionic compound, at least one cationic lipid selected from the group consisting of DOTIM, dimethyldioctadecyl ammonium bromide, 1,2 dioleyloxypropyl-3-trimethyl ammonium bromide, DOTAP, 1,2-dimyristyloxypropyl-3-dimethyl-hydroxyethyl ammonium bromide, EDMPC, and MBOP; and a neutral lipid selected from the group consisting of 1,2-dilauroyl-sn-glycero-3-phosphoethanolamine and 1,2diphytanoyl-sn-glycero-3-phosphoethanolamine.

2. A lipid complex according to claim 1 wherein the neutral lipid comprises 1,2-dilauroyl-sn-glycero-3-phosphoethanolamine.

3. A lipid complex according to claim 1 wherein the neutral lipid comprises 1,2-diphytanoyl-sn-glycero3-phosphoethanolamine.

4. A lipid complex according to claim 1 further characterized as having only one cationic lipid.

5. A lipid complex according to claim 3 wherein the cationic lipid and 1,2-dilauroyl-sn-glycero-3-phosphoethanolamine are present in a molar ratio ranging from about 1:3 to 3:1.

6. A lipid complex according to claim 5 wherein the cationic lipid and 1,2-dilauroyl-sn-glycero-3-phosphoethanolamine are present in a molar ratio of about 1:1.

7. A lipid complex according to claim 1 further characterized as being an SUV.

8. A lipid complex according to claim 1 further characterized as being an MLV.

9. A lipid complex according to claim 1 further characterized as being an LUV.

10. A transfection complex comprising a nucleic acid, a cationic lipid selected from the group consisting of DOTIM. dimethyldioctadecyl ammonium bromide, 1,2-dioleyloxypropyl-3-trimethyl ammonium bromide, DOTAP, 1,2-dimyristyloxyropyl-3-dimethyl-hydroxyethyl ammonium bromide. EDMPC, and MBOP; and a neutral lipid selected from the group consisting of 1,2-dilauroyl-sn-glycero-3-phosphoethanolamine and 1,2-diphytanoyl-sn-glycero-3-phosphoethanolamine.

11. A transfection complex according to claim 10 wherein the neutral lipid comprises [DLPE] 1,2-dilauroyl-sn-glycero-3-phosphoethanolamine.

12. A transfection complex according to claim 11 wherein the neutral lipid comprises [DiPPE] 1,2-diphytanoyl-sn-glycero-3-phosphoethanolamine.

13. A transfection complex according to claim 10 wherein the nucleic acid is DNA.

14. A transfection complex according to claim 10 wherein the nucleic acid is RNA.

15. A transfection complex according to claim 13 wherein the DNA encodes a therapeutic protein.

16. A transfection complex according the claim 14 wherein the RNA comprises antisense RNA.

17. A transfection complex according to claim 11 wherein the cationic lipid and [DLPE] 1,2-dilauroyl-sn-glycero-3-phosphoethanolamine are present in a molar ratio ranging from 1:3 to 3:1.

18. A transfection complex according to claim 10 further characterized as having a net positive charge.

19. A transfection complex according to claim 10 further characterized as having a net negative charge.

20. A transfection complex according to claim 11 wherein the cationic lipid and [DLPE] 1,2-dilauroyl-sn-glycero-3-phosphoethanolamine are present in a molar ratio of about 1:1.

21. A method of delivering a polyanion to a mammalian cell in vivo, comprising contacting said polyanion with a lipid carrier comprising a cationic lipid selected from the group consisting of DOTIM, dimethyldioctadecyl ammonium bromide, 1.2-dioleyloxypropyl-3-trimethyl ammonium bromide, DOTAP, 1,2-dimyristyloxypropyl-3-dimethyl-hydroxyethyl ammonium bromide, EDMPC, and MBOP: and a neutral lipid selected from the group consisting of 1,2-dilauroyl-sn-glycero-3-phosphoethanolamine and 1,2-diphytanoyl-sn-glycero-3-phosphoethanolamine to form a lipid/polyanion complex, and administering the lipid-polyanion complex to a mammal, whereby the polyanion is taken up by the mammalian cell.

22. The method according to claim 21 wherein the neutral lipid comprises [DLPE] 1,2-dilauroyl-sn-glycero-3-phosphoethanolamine.

23. The method according to claim 21 wherein the neutral lipid comprises [DiPPE] 1,2- diphytanoyl-sn-glycero3-phosphoethanolamine.

24. The method according to claim 21 wherein the polyanion is a nucleic acid.

25. The method according to claim 21 wherein said administering is by a method selected from the group consisting of intravenous, intraperitoneal, intradermal, subcutaneous, intramuscular, intratracheal, inhalation, topical and direct injection.

26. The method according to claim 24 wherein the nucleic acid is DNA.

27. The method according to claim 21 wherein the cationic lipid is DOTIM, the neutral lipid is [DLPE] 1,2-dilauroyl-sn-glycero-3-phosphoethanolamine and said administering is by intravenous administration.

28. The method according to claim 21 wherein the cationic lipid is EDMPC and said administering is by inhalation.

29. A method of transfecting a mammalian cell comprising contacting a polynucleotide with a lipid carrier comprising a cationic lipid selected from the group consisting of DOTIM, dimethyldioctadecyl ammonium bromide, 1,2-dioleyloxypropyl-3-trimethyl ammonium bromide, DOTAP, 1,2-dimyristyloxypropyl-3-dimethyl-hydroxyethyl ammonium bromide, EDMPC, and MBOP, and a neutral lipid selected from the group consisting of 1,2-dilauroyl-sn-glycero-3-phosphoethanolamine and 1,2-diphytanoyl-sn-glycero-3-phosphoethanolamine to form a transfection complex, and contacting said transfection complex with said mammalian cell.

30. The method of claim 29 wherein the neutral lipid comprises [DLPE] 1,2-dilauroyl-sn-glycero-3-phosphoethanolamine.

31. The method of claim 29 wherein the neutral lipid comprises [DiPPE] 1,2-diphytanoyl-sn-glycero-3-phosphoethanolamine.

32. The method according to claim 29 wherein said contacting is performed in vitro.

33. The method according to claim 29 wherein said contacting is performed in vivo.

34. The method according to claim 29 wherein said contacting is performed by intravenous administration.

35. The method according to claim 29 wherein said nucleic acid is plasmid DNA.

36. The method according to claim 29 wherein said nucleic acid is antisense RNA.

37. The method according to claim 30 cationic lipid and [DLPE] 1,2-dilauroyl-sn-glycero-3-phosphoethanolamine are present in a molar ratio ranging from about 1:3 to about 3:1.

38. A method of transfecting a mammalian cell in vivo comprising contacting a nucleic acid with a lipid carrier comprising a cationic lipid selected from the group consisting of DOTIM, dimethyldioctadecyl ammonium bromide, 1,2-dioleyloxypropyl-3-trimethyl ammonium bromide, DOTAP, 1,2-dimyristyloxypropyl-3-dimethyl-hydroxyethyl ammonium bromide, EDMPC, and MBOP; and 1,2-dilauroyl-sn-glycero-3-phosphoethanolamine to form a transfection complex, and administering said transfection complex to a mammal in vivo, whereby said mammalian cell is transfected.

39. The method according to claim 38 wherein said administering is by intravenous administration.

40. A method of transfecting a mammalian cell in vivo comprising contacting a nucleic acid with a lipid carrier comprising a cationic lipid selected from the group consisting of DOTIM, dimethyldioctadecyl ammonium bromide, 1,2-dioleyloxypropyl-3-trimethyl ammonium bromide, DOTAP, 1,2-dimyristyloxypropyl-3 -dimethyl-hydroxyethyl ammonium bromide, EDMPC, and MBOP; and 1,2-diphytanoyl-sn-glycero-3-phosphoethanolamine to form a transfection complex, and administering said transfection complex to a mammal in vivo, whereby said mammalian cell is transfected.

\* \* \* \* \*